(12) United States Patent
Bevot et al.

(10) Patent No.: US 9,983,157 B2
(45) Date of Patent: May 29, 2018

(54) CIRCUIT ASSEMBLY FOR OPERATING A GAS PROBE

(75) Inventors: Claudius Bevot, Stuttgart (DE); Helge Schichlein, Stuttgart (DE)

(73) Assignee: Robert Bosch GmbH, Stuttgart (DE)

(*) Notice: Subject to any disclaimer, the term of this patent is extended or adjusted under 35 U.S.C. 154(b) by 1268 days.

(21) Appl. No.: 13/704,650

(22) PCT Filed: Jun. 10, 2011

(86) PCT No.: PCT/EP2011/059739
§ 371 (c)(1),
(2), (4) Date: Dec. 17, 2012

(87) PCT Pub. No.: WO2012/007238
PCT Pub. Date: Jan. 19, 2012

(65) Prior Publication Data
US 2013/0081448 A1    Apr. 4, 2013

(30) Foreign Application Priority Data
Jun. 15, 2010  (DE) .................. 10 2010 030 117

(51) Int. Cl.
*G01N 27/00*    (2006.01)
*G01N 27/406*    (2006.01)
*G01N 27/419*    (2006.01)

(52) U.S. Cl.
CPC ......... *G01N 27/00* (2013.01); *G01N 27/4065* (2013.01); *G01N 27/419* (2013.01)

(58) Field of Classification Search
CPC ... G01N 27/00; G01N 27/419; G01N 27/4065
(Continued)

(56) References Cited

U.S. PATENT DOCUMENTS

| | | |
|---|---|---|
| 4,601,793 A | 7/1986 | Asayama et al. |
| 4,601,809 A | 7/1986 | Kitahara |

(Continued)

FOREIGN PATENT DOCUMENTS

| | | |
|---|---|---|
| CN | 101256162 | 9/2008 |
| JP | 2008058121 | 3/2008 |

OTHER PUBLICATIONS

PCT/EP2011/059739 International Search Report dated Jul. 9, 2011 (Translation and Original, 6 pages).

*Primary Examiner* — Hezron E Williams
*Assistant Examiner* — Truong D Phan
(74) *Attorney, Agent, or Firm* — Michael Best & Friedrich LLP

(57) ABSTRACT

The invention relates to a circuit assembly for operating a probe (10) for determining the oxygen concentration in a gas mixture, in particular a Lambda probe for determining the oxygen concentration in the exhaust gas of internal combustion engines, comprising two electrodes (11, 15) which act as an outer and an inner pump electrode and form a pump cell, two electrodes which act as a Nernst electrode (15) and a reference electrode (19) and form a Nernst cell, and a pump current controller (210), which controls a pump current that is applied to the pump cell such that a predeterminable Nernst voltage ($U_N$) that can be tapped at the Nernst cell is controlled to a predeterminable value, characterized in that the predeterminable value of the Nernst voltage can be varied.

9 Claims, 2 Drawing Sheets

(58) Field of Classification Search
USPC ......... 73/114.73, 23.31, 31.05; 204/406, 400
See application file for complete search history.

(56) References Cited

U.S. PATENT DOCUMENTS

| | | | |
|---|---|---|---|
| 4,614,175 A | | 9/1986 | Asayama |
| 4,753,203 A | | 6/1988 | Yamada |
| 5,837,114 A | * | 11/1998 | Junginger ............ G01N 27/419 123/672 |
| 2005/0000832 A1 | | 1/2005 | Holoch et al. |
| 2006/0137427 A1 | * | 6/2006 | Schnaibel et al. ............. 73/1.06 |
| 2007/0119719 A1 | * | 5/2007 | Diehl ........................ 205/785.5 |
| 2009/0114539 A1 | * | 5/2009 | Ziegler et al. ................ 204/424 |
| 2009/0145778 A1 | * | 6/2009 | Allmendinger ............... 205/789 |
| 2009/0242426 A1 | * | 10/2009 | Kilinc et al. .................. 205/781 |
| 2011/0314898 A1 | * | 12/2011 | Liemersdorf et al. ....... 73/23.31 |
| 2012/0266657 A1 | * | 10/2012 | Barnikow et al. ........... 73/31.05 |

\* cited by examiner

CIRCUIT ASSEMBLY FOR OPERATING A GAS PROBE

BACKGROUND OF THE INVENTION

The invention relates to a circuit assembly for operating a gas probe.

A so-called broad band Lambda probe and a circuit assembly for operating such a broadband Lambda probe is, for example, based on the book publication "Bosch Kraftfahrtechnisches Taschenbuch" ("Bosch Automotive Handbook"), 25. edition, October 2003, page 134. Such a probe embodied as a multilayer ceramic substantially consists of a combination of a conventional concentration probe (Nernst probe), which acts as a galvanic cell, and a limiting-current or "pump" cell. A voltage is externally applied to the pump cell. If the voltage is large enough, a so-called limiting current arises which is proportional to the difference between the oxygen concentrations on both sides of the probe. Oxygen ions are transported—as a function of polarity—with the current. The circuit assembly, which constitutes an electronic regulating circuit, ensures that the concentration probe is always supplied by the pump cell via a very narrow diffusion gap with exactly as much oxygen from the exhaust gas that the state Lambda=1 prevails at said probe. In the case of an excess of air in the exhaust, in the so-called lean range, oxygen is pumped off; whereas in the case of a small residual oxygen content in the exhaust gas, i.e. in the rich range, oxygen is supplied to said concentration probe by reversing the pump voltage. The pump current thereby forms the output signal of the probe.

In the case of such two-cell broadband Lambda probes, a constant nominal (Nernst) voltage is predetermined, which amounts to at least 450 mV. This constant voltage serves as the nominal value for a pump current controller. The pump current controller has the task of controlling the Nernst cell voltage to the desired, constant nominal value by varying the level and polarity of the pump current.

This control of the Nernst voltage to a constant value requires a defined operating point of the probe, an operating point whereat the probe works properly and which is characterized, for example, by a nominal operating temperature. If, for example, said nominal operating temperature is not achieved, a proper operation of the probe is not ensured. When the operating temperature is undershot, oscillations of the pump current controller can then, for example, occur as a result of controlling the Nernst voltage to a constant value.

SUMMARY OF THE INVENTION

Advantages of the Invention

The inventive circuit assembly has in contrast the advantage that the probe can be operated over a wide operating range, particularly, for example, even in the case where the nominal operating temperature has not yet been achieved. The probe has then a temperature which is lower than the nominal operating temperature.

A stable operation is ensured even in this case by virtue of the fact that the predeterminable value of the Nernst voltage is not specifically predetermined but can be varied. An adaptation of the operating method of the probe to the predetermined boundary conditions is thereby possible to a certain extent.

Provision is thus made in an advantageous embodiment for the predeterminable value of the Nernst voltage to be varied as a function of the operating point. In so doing, the Nernst voltage is adapted as a function of the operating point.

The predeterminable value of the Nernst voltage is advantageously varied as a function of at least the probe temperature and/or the composition of the gas mixture.

The variation can thereby take place continuously in an expedient manner, i.e. the predeterminable value of the Nernst voltage is continuously varied. In so doing, the probe can be adjusted to a wide range of operating points.

Another embodiment provides for the predeterminable values of the Nernst voltage to be varied in steps to at least two voltage values.

In the case of the nominal operating temperature of the probe not being achieved, an embodiment of the invention provides for the predeterminable values of the Nernst voltage to be reduced, in particular from 450 mV to 200 mV, when the nominal operating temperature of the probe is undershot.

BRIEF DESCRIPTION OF THE DRAWINGS

Exemplary embodiments of the invention are depicted in the drawings and are explained in detail in the following description. The features can thereby be implemented by themselves or in combination.

In the drawings.

DETAILED DESCRIPTION

Figure 1:
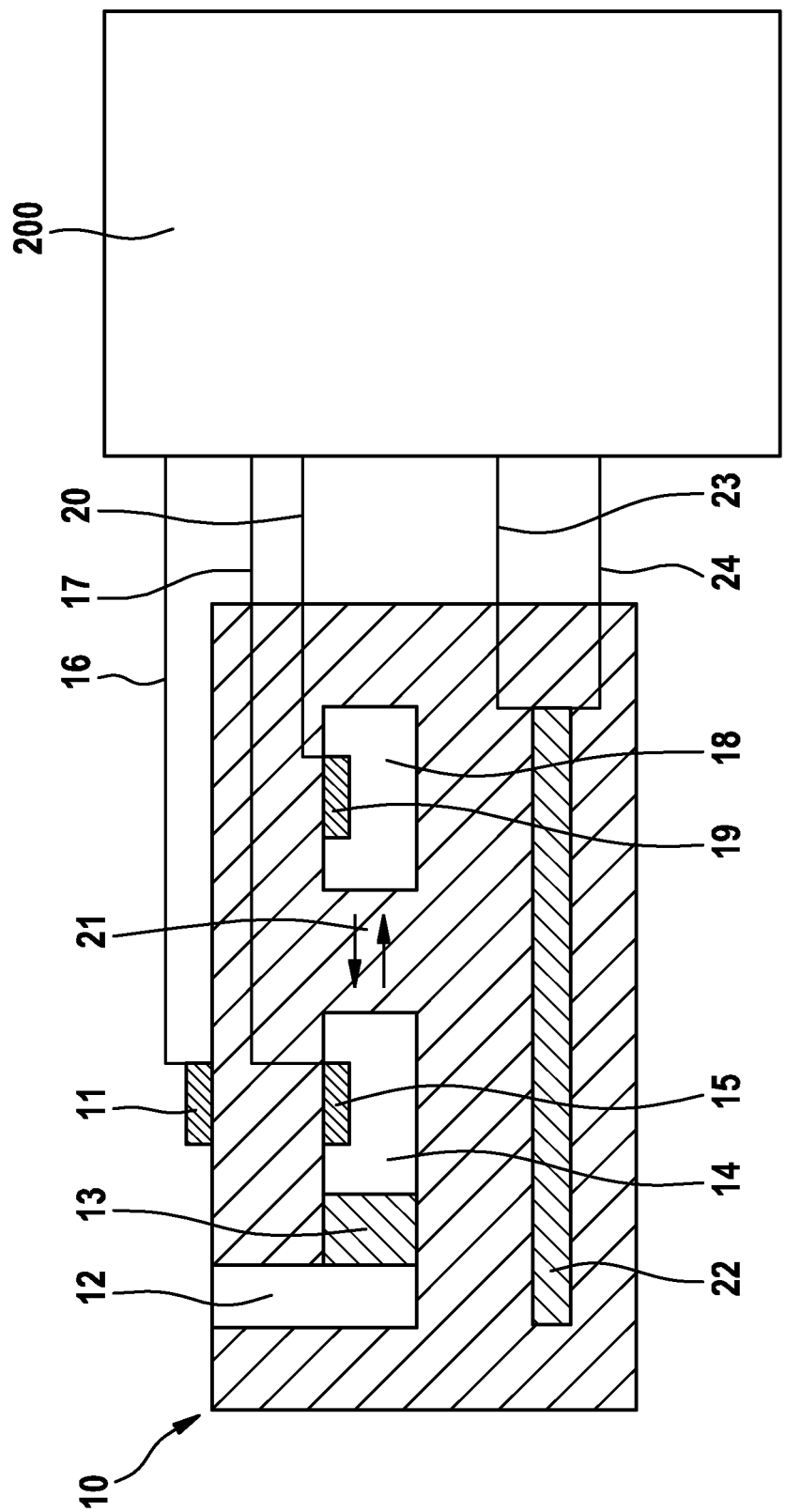
FIG. 1 shows schematically a sensor element of a gas sensor comprising a circuit assembly and FIG. 2 shows the equivalent circuit diagram of the gas sensor comprising a circuit assembly.

The gas sensor 10 shown schematically in FIG. 1 comprises a first electrode, which is also called the outer pump electrode and is exposed to the gas to be tested. The gas to be tested travels over a gas channel 12 and a diffusion barrier 13 into a measuring gas chamber 14, in which a second electrode, also called the inner pump electrode 15, is disposed. A pump cell is formed between the first and the second electrode 11, 15. The first electrode 11 is connected to a pump current line 16 and the second electrode 15 to a measurement line 17.

The gas sensor 10 comprises a reference gas chamber 18, in which a third electrode, also referred to as the reference electrode 19, is disposed, said third electrode being connected to a reference pump current line 20. A Nernst cell having a Nernst voltage $U_N$, in which a reference gas ion transport 21 can take place, is formed between the reference gas chamber 18 and the measuring gas chamber 14 exactly in the same way as between the electrodes 11, 15. The Nernst voltage $U_N$ can be tapped between the lines 17 and 20.

Figure 2:
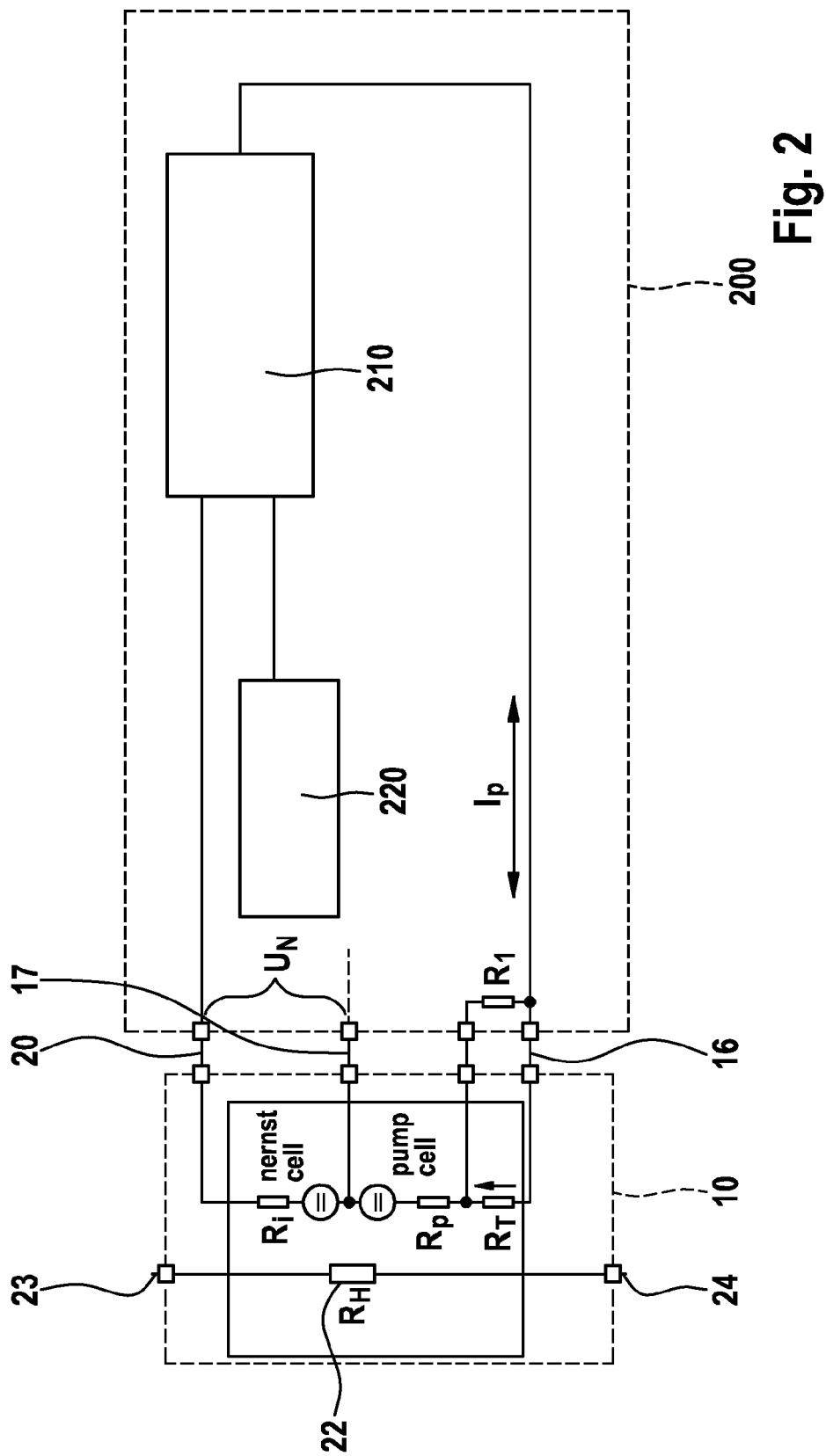

An equivalent circuit diagram of a gas sensor of this kind as well as a detailed configuration of the circuit assembly 200, which is, for example, part of a control device of an internal combustion engine, is depicted schematically in FIG. 2. Identical elements are thereby denoted with the identical reference numerals as in FIG. 1. The sensor heater 22 is denoted in FIG. 2 as the resistor RH and the heating cables 23, 24 can be attached to terminal or plug contacts. The Nernst cell is depicted schematically as an equivalent circuit diagram consisting of a resistor $R_i$ and a voltage source. The pump cell is likewise depicted as an equivalent circuit diagram consisting of a voltage source and a resistor $R_p$. A Trimm resistor $R_T$ can also be disposed in the sensor, which lies parallel to a resistor R1 disposed in the circuit assembly 200 and serves to adjust the probe in a manner which is known per se and not described here.

The circuit assembly 200 comprises a pump current controller 210, which can be designed with analog or digital circuitry. Said pump current controller 210 serves to adjust the pump current $I_p$ which is applied to the probe 10. The pump current $I_p$ is supplied in this case via the pump current line 16 and the reference pump current line 20. In the case of probes known from prior art, the adjustment of the pump current takes place as a function of a predeterminable value of the Nernst voltage, which for the most part amounts to 450 mV. This constant voltage serves as a nominal value for the pump current controller 210. Said pump current controller has the task of controlling the Nernst cell voltage to a desired constant nominal value by varying the pump current $I_p$ with regard to the level and polarity thereof. The situation can now arise that the probe 10 has, for example, still not yet achieved the nominal operating temperature thereof. In this case, a stable operation of the probe 10 is not ensured, but on the contrary such a control leads to oscillations of the pump current controller 210.

The basic idea of the invention is therefore no longer to adjust the Nernst voltage $U_N$ to a constant predeterminable value with the aid of the pump current controller but to predefine a variable value of the Nernst nominal voltage. This is schematically depicted by the circuit unit 220. The voltage can, e.g., be varied as a function of parameters, for example, dependent on the probe temperature or the composition of the gas mixture. The voltage can be varied continuously as well as in steps via two or several constant values as a function of said parameters.

By varying the nominal voltage, i.e. the predeterminable value of the Nernst voltage, in this way, a stable operation of the probe 10 can be ensured at operating points having special boundary conditions. For example, a stable operation of the probe 10 can be ensured in the case of a cold probe, the temperature of which is lower than the nominal operating temperature, if the nominal voltage, i.e. the predeterminable value of the Nernst voltage, is reduced, e.g., from 450 mV to 200 mV. In this instance, the reduction of the predeterminable value of the Nernst voltage takes place in the circuit unit 220, and the pump current controller adjusts a corresponding pump current $I_p$. It should be noted that besides taking on a discrete analog or digital design, the pump current controller can also be implemented as a computer program in a control unit of the internal combustion engine.

The invention claimed is:

1. A circuit assembly for operating a probe (10) for determining the oxygen concentration in a gas mixture comprising a pump cell having two electrodes (11, 15), as an outer and an inner pump electrode, a Nernst cell having two electrodes, a Nernst electrode (15) and a reference electrode (19), and a pump current controller (210), which controls a pump current that is applied to the pump cell such that a predeterminable Nernst voltage ($U_N$), that can be tapped at the Nernst cell, is controlled to a predeterminable value, characterized in that the predeterminable value of the Nernst voltage is varied.

2. The circuit assembly according to claim 1, characterized in that the predeterminable value of the Nernst voltage is varied as a function of an operating point.

3. The circuit assembly according to claim 1, characterized in that the predeterminable value is continuously varied.

4. The circuit assembly according to claim 1, characterized in that the predeterminable value of the Nernst voltage is controlled in steps to at least two voltage values.

5. The circuit assembly according to claim 1, characterized in that the predeterminable value of the Nernst voltage is varied as a function of the probe temperature.

6. The circuit assembly according to claim 1, characterized in that the predeterminable value of the Nernst voltage is varied as a function of the composition of the gas mixture.

7. The circuit assembly according to claim 1, characterized in that the predeterminable value of the Nernst voltage is varied as a function of the probe temperature and the composition of the gas mixture.

8. The circuit assembly according to claim 7, characterized in that the predeterminable value of the Nernst voltage is reduced if a nominal operating temperature of the probe is undershot.

9. The circuit assembly according to claim 8, characterized in that the predeterminable value of the Nernst voltage is reduced from 450 mV to 200 mV if a nominal operating temperature of the probe is undershot.

* * * * *